United States Patent [19]

Jackson et al.

[11] 4,115,645

[45] Sep. 19, 1978

[54] DECOLORIZING PROCESS FOR 7-AMINO-3-(((2-METHYL-1,3,4-THIADIAZOL-5-YL)THIO)METHYL)-3-CEPHEM-4-CARBOXYLIC ACID

[75] Inventors: Billy G. Jackson, Indianapolis; Roger E. McPherson, Lafayette, both of Ind.

[73] Assignee: Eli Lilly and Company, Indianapolis, Ind.

[21] Appl. No.: 795,464

[22] Filed: May 10, 1977

[51] Int. Cl.$^2$ ............................................. C07D 501/12
[52] U.S. Cl. ..................................................... 544/20
[58] Field of Search ...................... 260/243 C; 544/20

[56] References Cited

U.S. PATENT DOCUMENTS

| 3,278,531 | 10/1976 | Cox et al. | 260/243 C |
| 3,516,997 | 6/1970 | Takano et al. | 260/243 C |
| 3,979,383 | 9/1976 | Wild | 260/243 C |

FOREIGN PATENT DOCUMENTS 809,060   12/1973   Belgium ............................. 260/243 C

*Primary Examiner*—Nicholas S. Rizzo
*Attorney, Agent, or Firm*—Kathleen R. S. Page; Arthur R. Whale

[57] ABSTRACT

The present invention is directed to the use of sodium sulfite and sodium dithionite for the decolorization of 7-amino-3-(((2-methyl-1,3,4-thiadiazol-5-yl)thio)methyl)-3-cephem-4-carboxylic acid.

7 Claims, No Drawings

DECOLORIZING PROCESS FOR 7-AMINO-3-(((2-METHYL-1,3,4-THIADIAZOL-5-YL)THIO)METHYL)-3-CEPHEM-4-CARBOXYLIC ACID

SUMMARY

The compound 7-(2-(1H-tetrazol-1-yl)acetamido)-3-(((2-methyl-1,3,4-thiadiazol-5-yl)thio)methyl)-3-cephem-4-carboxylic acid, also called cefazolin, has the formula

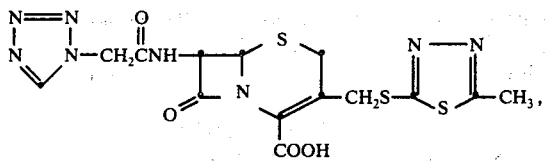

and is a known antibiotic (see, e.g. U.S. Pat. No. 3,516,997, Example 18(b)). It is prepared, in one synthetic route, by the nucleophilic displacement of the 3-acetoxy group from 7-ACA, followed by acylation of the 7-position. However, the displacement reaction is accompanied by formation of highly colored impurities, which if not removed contaminate the ultimate product, cefazolin.

These impurities can be removed by the process described in U.S. Pat. No. 3,979,383, in which process a solution of a compound such as 7-amino-3-(((2-methyl-1,3,4-thiadiazol-5-yl)thio)methyl)-3-cephem-4-carboxylic acid is chromatographed over an anion exchange resin such as Amberlite IRA-458. However, while this process is effective in removing the impurities, it generates large volumes of waste water requiring subsequent disposal. Also, not all of the product is recoverable from the resin, so that there is a slight reduction in yield.

The present process provides an improved method for treating 7-amino-3-(((2-methyl-1,3,4-thiadiazol-5-yl)thio)methyl)-3-cephem-4-carboxylic acid. In the present process, sodium sulfite or sodium dithionite is employed to decolorize impurities in 7-amino-3-(((2-methyl-1,3,4-thiadiazol-5-yl)thio)methyl)-3-cephem-4-carboxylic acid. The process can be carried out without generating additional volumes of waste liquid and with only minimal reduction in yield.

DETAILED DESCRIPTION OF INVENTION

Most broadly, the present invention is directed to a process for decolorizing impurities associated with 7-amino-3-(((2-methyl-1,3,4-thiadiazol-5-yl)thio)methyl)-3-cephem-4-carboxylic acid or a salt thereof, which comprises adding a reducing agent selected from the class consisting of sodium sulfite and sodium dithionite to an aqueous solution of a salt of 7-amino-3-(((2-methyl-1,3,4-thiadiazol-5-yl)thio)methyl)-3-cephem-4-carboxylic acid and colored impurities, and thereafter recovering decolorized 7-amino-3-(((2-methyl-1,3,4-thiadiazol-5-yl)thio)methyl-3-cephem-4-carboxylic acid or a salt thereof.

In one embodiment, the 7-amino-3-(((2-methyl-1,3,4-thiadiazol-5-yl)thio)methyl)-3-cephem-4-carboxylic acid is converted to a water soluble salt, such as the sodium or ammonium salt, in aqueous solution, and the sodium sulfite or sodium dithionite is then added. After decolorization has occurred, the 7-amino-3-(((2-methyl-1,3,4-thiadiazol-5-yl)thio)methyl)-3-cephem-4-carboxylic acid or a salt thereof is recovered in conventional procedures.

In another, preferred embodiment of the present invention, decolorization is carried out in the reaction mixture in which the 7-amino-3-(((2-methyl-1,3,4-thiadiazol-5-yl)thio)methyl)-3-cephem-4-carboxylic acid or a salt thereof has been, or is being, prepared. This embodiment avoids the necessity for a separate decolorization step. In this embodiment, the present invention is an improvement on the prior art process for the preparation of 7-amino-3-(((2-methyl-1,3,4-thiadiazol-5-yl)thio)methyl)-3-cephem-4-carboxylic acid or a salt thereof by the displacement of the acetoxy group from 7-ACA (7-aminocephalosporanic acid) with 5-methyl-1,3,4-thiadiazole-2-thiol.

In this embodiment, conventional displacement reaction conditions are employed. Accordingly, the reaction is typically conducted in an aqueous medium, adjusted to a pH of 5–8, preferably 7–8; at temperatures of 70°–75° C., and with a slight excess of the 5-methyl-1,3,4-thiadiazole-2-thiol reactant.

The reducing agent to be employed in accordance with the present invention is added to this reaction mixture. The time at which the addition is made is not critical. The reducing agent can be added with either of the reactants, to the reaction mixture after the reactants have been brought together, or to the reaction mixture after the reaction is essentially complete. The reducing agent can be split into two portions and added at different stages of the reaction. This practice has been found to be advantageous.

The amount of reducing agent employed is not critical. In general, good results are obtained when employing from 0.5 to 1.5 moles of sodium sulfite per mole of 7-ACA; or from 0.1 to 0.6 mole of sodium dithionite per mole of 7-ACA. For maximum decolorization with minimum reducing agent, from 0.85 to 1.15 moles of sodium sulfite, or from 0.15 to 0.25 mole of sodium dithionite, per mole of 7-ACA, have been found satisfactory.

Since sodium sulfite and sodium dithionite react with the oxygen in air, it is preferred for maximum efficiency that the decolorization be conducted under a stream of nitrogen or with nitrogen purging of the solution.

Whether conducted as a separate step or as part of the reaction by which 7-amino-3-(((2-methyl-1,3,4-thiadiazol-5-yl)thio)methyl)-3-cephem-4-carboxylic acid is prepared, the present decolorization is carried out in an aqueous medium. Small amounts of an organic solvent are not deleterious, however; for example, 7-ACA is often produced as an acetone-wet product, and this product can be employed directly in a displacement reaction under the conditions of the present invention.

The following examples illustrate the present invention and will enable those skilled in the art to practice the invention.

In these examples, unless otherwise indicated, analysis of color was made by determining optical density at 500 nm in the visible spectrum on a 0.5 percent solution of the compound being evaluated. Also in these examples, stated amounts of 7-ACA represent 7-ACA only, after correction for minor amounts of impurities.

EXAMPLE 1

Use of Sodium Sulfite, Added to Reaction Mixture With 7-ACA

Under a nitrogen purge, 400 ml. of water, 30 ml. of acetone, 28.2 grams of 7-ACA (about 0.10 mole), and 13.1 grams of sodium sulfite (representing 1 mole per mole of 7-ACA) were mixed. The acetone was employed to simulate acetone-wet 7-ACA as a starting material. Ammonium hydroxide was added to dissolve all of the solids (pH = about 7.6 at room temperature).

Separately, also under a nitrogen purge, 800 ml. of water, and 16 grams of 5-methyl-1,3,4-thiadiazole-2-thiol (about 0.12 mole) were mixed and heated to 65° C. Ammonium hydroxide was added to dissolve all solids, pH = about 7.0.

The two solutions were combined with a nitrogen purge being continued throughout. The temperature of the reaction mixture fell and the reaction mixture was heated back to 65° C. and maintained as 64°-67° C. with stirring for 70 minutes. Ammonium hydroxide was added as necessary to maintain the pH at 6.6-6.9.

The reaction mixture was treated with HCl to bring the pH to 4.0, cooled to 0° C., stirred 30 minutes, filtered, washed with 200 ml. of water, washed with 200 ml. of acetone, washed with 100 ml. of acetone, and vacuum dried at 45° C. Yield was 72.3 percent and color was rated at 0.011.

EXAMPLE 2

Use of Sodium Sulfite, Added to Reaction Mixture With Both Reactants, Varying Amounts of Sodium Sulfite Each reaction was conducted as described below.

A nitrogen purge ws used throughout. Deionized water (400 ml.), acetone-wet 7-ACA (80.0 grams, representing 28.2 grams and about 0.1 mole of 7-ACA), and one-half of the total amount of sodium sulfite in those reactions utilizing the same were mixed and the pH adjusted to 7.8 with 28 percent ammonium hydroxide.

A separate solution was prepared by mixing deionized water heated to 65°-67° C. (800 ml.), 5-methyl-1,3,4-thiadiazole-2-thiol (16 grams; about 0.12 mole), and the remaining amount of sodium sulfite in those reactions utilizing the same. The pH was adjusted to pH 6.5-7.0 with 28 percent ammonium hydroxide.

The former solution was added to the latter solution and the temperature allowed to rise to 65°-67° C. It was maintained at that temperature and at pH of 6.5-7.0 for 70 minutes with stirring. The pH was adjusted to 4.0 with HCl, then cooled to 0°-5° C. The nitrogen purge was removed. The reaction mixture was then stirred one-half hour at 0°-5° C., filtered, washed with 200 ml. of deionized water, washed with 200 ml. of acetone, and dried in a 45° vacuum oven.

The results were as set forth in the following table:

| Grams of sodium sulfite employed | Mole(s) of sodium sulfite/mole of 7-ACA | Yield in grams | Percent yield* | Color |
|---|---|---|---|---|
| (control) | — | 31.8 | 82.3 | 0.192 |
| 6.50 | 0.5 | 31.0 | 81.4 | 0.028 |
| 19.6 | 1.5 | 30.2 | 78.0 | 0.009 |

*Corrected for starting materials.

EXAMPLE 3

Use of Sodium Dithionite, Added After Reaction Complete

7-ACA (13.4 grams; 0.05 mole) was added to 200 ml. of water and 3.9 ml. of concentrated ammonium hydroxide was added; the pH of the resulting solution was 7.75. A separate solution was prepared by adding 16.0 grams of 5-methyl-1,3,4-thiadiazole-2-thiol (0.12 mole) to 400 ml. of water followed by 8.0 ml. of concentrated ammonium hydroxide (pH = 7). The latter solution was heated to 65° C. and the former solution was added over a period of 14 minutes, keeping the temperature at 63°-65° C. The reaction mixture was then stirred for 70 minutes at 65° C. The reaction mixture was dark in color.

Sodium dithionite (5.0 grams; 0.029 mole; equivalent to 0.57 mole per mole of 7-ACA) was added and the solution was stirred for 5 minutes at 60°-65° C. The solution became much lighter. HCl was added at 60°-65° C. to pH 4.0, and the mixture was then cooled to room temperature and the pH rechecked (it was still 4.0). The mixture was then cooled to <5° C. and stirred at <5° C. for 15 minutes. The product was separated by filtration, rinsed with water and acetone and vacuum dried at about 50° C. The yield was 14.7 grams, and color was rated at 0.038.

EXAMPLE 4

Use of Sodium Dithionite, Added in Two Portions

7-ACA (13.4 grams; 0.05 mole) was stirred in 200 ml. of water and 4.3 ml. of concentrated ammonium hydroxide added to dissolve the 7-ACA. In a separate solution, 16.0 grams of 5-methyl-1,3,4-thiadiazole-2-thiol (0.12 mole), 400 ml. of water, and 8.2 ml. of concentrated ammonium hydroxide were stirred together until the thiol was dissolved (pH = 7). The latter solution was heated to 65° C. and the former solution of 7-ACA was added over a period of 13 minutes. The temperature during the addition was 64.0°-65.5° C. The resulting reaction mixture was stirred and 2.5 grams of sodium dithionite added. The color of the reaction mixture lightened.

The reaction mixture was then stirred at 65° ± 1° C. for 70 minutes. The color of the reaction mixture darkened somewhat during this period. Heating was discontinued and 2.5 more grams of sodium dithionite (total of 0.029 mole and 0.57 mole per mole of 7-ACA) was added. The mixture turned green. It was stirred for 15 minutes during which the temperature fell to 61° C. and the color lightened to a lemon yellow. Concentrated HCl was added to bring the pH to 3.8 (11.5 ml.). The mixture was cooled to 25° and the pH rechecked (3.7). The mixture was then cooled to 20° and stored in a refrigerator overnight, about 16 hours. The product was then separated by filtration, rinsed with water and acetone, evaporated to a damp state, and reslurried in 150 ml. of acetone for 5 minutes. The product was again separated by filtration, washed successively with acetone, water, and acetone, and vacuum dried at about 50° C. Yield was 12.5 grams (73.3 percent). Color was rated at 0.000 (a 0.5 percent solution) and at 0.012 (a 2.0 percent solution).

EXAMPLE 5

Use of Sodium Dithionite, Acetone-wet 7-ACA

400ml. of water was stirred and swept with a slow stream of nitrogen for 30 minutes at room temperature. 5-Methyl-1,3,4-thiadiazole-2-thiol (9.3 grams; 0.07 mole) and 4.8 ml. of concentrated ammonium hydroxide were added and the mixture warmed to 35° C. (pH = 7). Separately, 42.2 grams of acetone-wet 7-ACA (representing 14.1 grams of 7-ACA (0.052 mole)) was stirred into 200 ml. of water. Concentrated ammonium hydroxide (4.0 ml.) was added dropwise to dissolve the 7-ACA (pH = 8.0). The former solution was heated to 65° C. and 0.3 gram of sodium dithionite was added to the solution of 7-ACA and stirred for 2 minutes. The 7-ACA solution with the sodium dithionite was then added to the solution containing 5-methyl-1,3,4-thiadiazole-2-thiol, at 64°–66° C. The resulting mixture was a pale straw color and was hazy.

The reaction mixture was heated at 65° ± 1° C. for 70 minutes; a slow stream of nitrogen was fed through the reaction mixture during this period. The reaction mixture was then a slightly deeper shade of yellow. Sodium dithionite (1.0 gram; a total of 0.007 mole and 0.14 mole per mole of 7-ACA) was added and the solution stirred with a nitrogen sweep over the surface and heating discontinued. The temperature after 15 minutes was 61° C. and the pH 6.5.

Concentrated HCl was added (8.6 ml.) to bring the pH to 4.0. The solution was cooled to <5° C. and stirred at <5° C. for 35 minutes. The product crystallized and was filtered; rinsed successively with water, acetone, and acetone; and vacuum dried at about 50° C.

The yield was 13.6 grams (80.0 percent yield). Color was rated at 0.008.

EXAMPLE 6

Use of Sodium Dithionite, Acetone-wet 7-ACA, Filration Step Added

The procedures reported in Example 5 were repeated with this modification: 3 grams of Hyflo (a diatomaceous earth filter aid) were added to the solution of 7-ACA, and the solution was filtered through a filter pad of 3 more grams of Hyflo (prior to addition to the thiol solution). Haziness in the solution was removed by this procedure.

Yield was 13.3 grams (78.0 percent yield). Color was rated at 0.013.

EXAMPLE 7

Use of Sodium Dithionite, Slower HCl Addition

The procedures reported in Example 6 were repeated except that the HCl was added over a period of 10 minutes instead of 1 minute as in Example 5. The product was visibly lighter in color. Yield was 13.7 grams (77.1 percent yield). Color was rated at 0.005.

EXAMPLE 8

Use of Sodium Dithionite, Preferred Conditions

Acetone-wet 7-ACA (44.2 grams, representing 14.1 grams and 0.052 mole of 7-ACA) was stirred with 200 ml. of water and ammonium hydroxide added dropwise to dissolve the 7-ACA, 4.1 ml. over 30 minutes (pH = 7.75). About 3 grams of Hyflo were added and the mixture was filtered through a filter pad of about 3 more grams of Hyflo. The vessel and filter pad were rinsed with about 15 ml. of 0.01 M sodium bicarbonate solution. The filtrate was nearly clear and had a pH = 7.5. Separately, 400 ml. of water were purged with a slow stream of nitrogen for 1½ hours; 8.0 grams of 5-methyl-1,3,4-thiadiazole-2-thiol (0.06 mole) and 4.3 ml. of concentrated ammonium hydroxide were added and the mixture heated to dissolve the thiol, pH = about 7 at about 40° C.

To the solution of 7-ACA there was added 0.3 gram of sodium dithionite. The pH fell to 7.35. The resulting solution of 7-ACA and sodium dithionite was added in one portion to the solution of the thiol at 65° C. A nitrogen purge was continued throughout the rest of the experiment.

The reaction mixture was heated back to 65° C. (7 minutes), then stirred at 65° ± 1° C. for 75 minutes. An additional 2.0 grams of sodium dithionite was added (total of 0.013 mole and 0.25 mole of sodium dithionite per mole of 7-ACA), the heat was turned off and the reaction mixture was stirred for 15 minutes, giving a terminal temperature of 60.5° C. and pH = 6.4. Concentrated HCl was added over 5 minutes to pH 3.95 (8.8 ml. of HCl). The mixture was cooled to 25° C., pH = 3.85, then cooled to <5° C. and stirred at <5° C. for 30 minutes. Product was separated by filtration.

Yield was 13.9 grams (78.2 percent). Color was rated at 0.000 (500 nm) and at 0.025 (450 nm).

EXAMPLE 9

Comparison of Sodium Sulfite and Sodium Dithionite

7-ACA (14.1 grams; 0.052 mole) was stirred with 200 ml. of water and 6.52 grams of sodium sulfite (0.05 mole and about 1 mole of sodium sulfite per mole of 7-ACA) added. Concentrated ammonium hydroxide was added to dissolve the 7-ACA (4.0 ml.).

Separately, 400 ml. of water was stirred and purged for 2 hours with a slow stream of nitrogen. Then 5-methyl-1,3,4-thiadiazole-2-thiol (11.0 grams; 0.08 mole) and 6.2 ml. of concentrated ammonium hydroxide were added. The mixture was warmed to dissolve the thiol, pH = 7-8.

The thiol solution was warmed to 65° C. and the 7-ACA and sulfite solution added in one portion. The temperature fell to 52° C. and the reaction mixture was heated back to 65° C. in 5 minutes. The mixture was then stirred at 65° ± 1° C. for 75 minutes, maintaining the nitrogen purge. The reaction mixture was more orange in color than where sodium dithionite was used.

Heating was discontinued and the reaction mixture stirred for 15 minutes; the temperature fell to 61° C. and the color deepened somewhat, pH = 7.2. Concentrated HCl was added during 9 min. to pH 3.9 (12.2 ml). The mixture was cooled to 25° C., pH = 3.85, then cooled to <5° C. and stirred at <5° C. for 30 minutes. The product was filtered, rinsed with water and acetone, vacuum dried, and slurried in 150 ml. acetone. The product was separated, washed with acetone, water, and acetone, and vacuum dried at about 50° C.

Yield was 14.4 grams (80.9 percent). Color was rated at 0.010.

The same reaction was carried out in essentially the same procedures except that 0.3 gram of sodium dithionite (0.0017 mole, about 0.03 mole of sodium dithionite per mole of 7-ACA) was employed in lieu of the sodium sulfite.

Yield was 14.4 grams (80.9 percent). Color was rated at 0.000 (500 nm) and 0.027 (450 nm).

We claim:

1. A process for decolorizing impurities associated with 7-amino-3-(((2-methyl-1,3,4-thiadiazol-5-yl)thio)-methyl)-3-cephem-4-carboxylic acid or a salt thereof, which comprises (1) adding a reducing agent selected from the group consisting of sodium sulfite and sodium dithionite to an aqueous solution of a salt of 7-amino-3-(((2-methyl-1,3,4-thiadiazol-5-yl)thio)methyl)-3-cephem-4-carboxylic acid and colored impurities, and (2) recovering decolorized 7-amino-3-(((2-methyl-1,3,4-thiadiazol-5-yl)thio)methyl)-3-cephem-4-carboxylic acid or a salt thereof from the solution.

2. The process of claim 1 in which the solution of a salt of 7-amino-3-(((2-methyl-1,3,4-thiadiazol-5-yl)thio)-methyl)-3-cephem-4-carboxylic acid and colored impurities is one in which the salt of 7-amino-3-(((2-methyl-1,3,4-thiadiazol-5-yl)thio)methyl)-3-cephem-4-carboxylic acid has been prepared by nucleophilic displacement of the acetoxy of 7-aminocephalosporanic acid by 5-methyl-1,3,4-thiadiazole-2-thiol.

3. The process of claim 2 in which the reducing agent is sodium sulfite.

4. The process of claim 2 in which the reducing agent is sodium dithionite.

5. In a process for the preparation of 7-amino-3-(((2-methyl-1,3,4-thiadiazol-5-yl)thiol)methyl)-3-cephem-4-carboxylic acid or a salt thereof by nucleophilic displacement of the acetoxy group of 7-aminocephalosporanic acid with 5-methyl-1,3,4-thiadiazole-2-thiol in an aqueous solution, the improvement which comprises conducting the displacement in the presence of a reducing agent selected from the group consisting of sodium sulfite and sodium dithionite.

6. The process of claim 5 in which the reducing agent is sodium sulfite.

7. The process of claim 5 in which the reducing agent is sodium dithionite.

* * * * *